United States Patent [19]

Suzuki et al.

[11] Patent Number: 4,718,999
[45] Date of Patent: Jan. 12, 1988

[54] AIR-FUEL RATIO DETECTOR

[75] Inventors: Seiko Suzuki, Hitachiohta; Masayuki Miki, Katsuta; Takao Sasayama; Toshitaka Suzuki, both of Hitachi; Nobuo Sato, Iwaki; Sadayasu Ueno, Katsuta; Akira Ikegami, Hitachi, all of Japan

[73] Assignee: Hitachi, Ltd., Tokyo, Japan

[21] Appl. No.: 764,070

[22] Filed: Aug. 9, 1985

[30] Foreign Application Priority Data

Aug. 13, 1984 [JP] Japan .................. 59-167854

[51] Int. Cl.[4] .......................................... G01N 27/56
[52] U.S. Cl. ................... 204/406; 204/410; 204/412; 204/425; 204/426
[58] Field of Search ................ 204/424–429, 204/412, 406, 410

[56] References Cited

U.S. PATENT DOCUMENTS

| 4,224,113 | 9/1980 | Kimurz et al. | 204/425 |
| 4,264,425 | 4/1981 | Kimura et al. | 204/425 |
| 4,292,158 | 9/1981 | Müller et al. | 204/425 |
| 4,298,573 | 11/1981 | Fujishiro | 204/425 |
| 4,300,991 | 11/1981 | Chiba et al. | 204/426 |
| 4,306,957 | 12/1981 | Ishitani et al. | 204/426 |
| 4,394,222 | 7/1983 | Rohr | 204/427 |
| 4,440,621 | 4/1984 | Kitahara et al. | 204/425 |
| 4,450,065 | 5/1984 | Yamada et al. | 204/425 |
| 4,452,687 | 6/1984 | Torisu et al. | 204/425 |
| 4,570,479 | 2/1986 | Sakurai et al. | 204/426 |
| 4,574,627 | 3/1986 | Sakurai et al. | 204/426 |

FOREIGN PATENT DOCUMENTS 0192853 11/1982 Japan ....................... 204/426

Primary Examiner—John F. Niebling
Assistant Examiner—Ben C. Hsing
Attorney, Agent, or Firm—Antonelli, Terry & Wands

[57] ABSTRACT

An air-fuel ratio in the lean range is detected by measuring a limiting current when oxygen diffused to a first electrode is pumped to a second electrode via a solid electrolyte. A stoichiometric air-fuel ratio is detected from electromotive force between first and third electrodes when oxygen is pumped from the first electrode to the third electrode. The invention is characterized by use of such three electrodes. Furthermore, an air-fuel ratio in a rich range is detected by either sending oxygen from the first electrode to the third electrode via the solid electrolyte and measuring a current when the electromotive force between the first and third electrodes is controlled to be constant, or measuring a current when the air-fuel ratio range is judged as "rich" from this electromotive force and the polarity of the impressed voltage at the time of lean detection is reversed.

17 Claims, 34 Drawing Figures

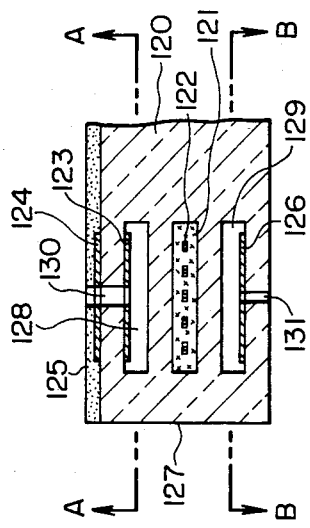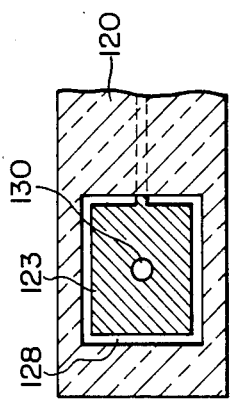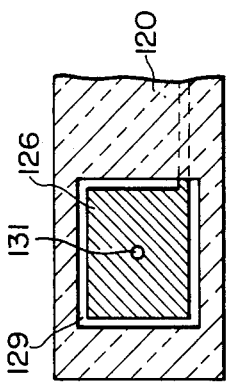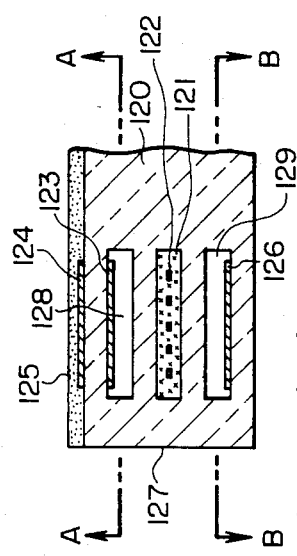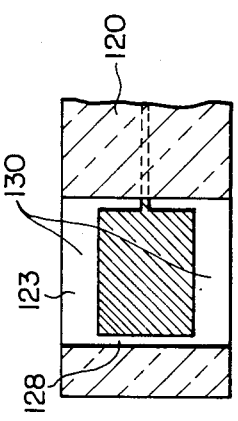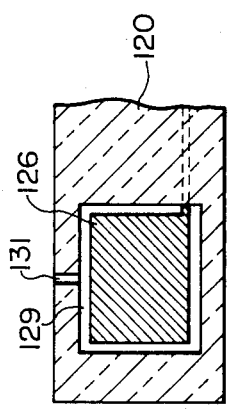
FIG. 10(a)  FIG. 10(b)  FIG. 10(c)
FIG. 9(a)  FIG. 9(b)  FIG. 9(c)

AIR-FUEL RATIO DETECTOR

BACKGROUND OF THE INVENTION

This invention relates to an air-fuel ratio detector which detects the air-fuel ratio of the presently operating state of an internal combustion engine of an automobile from exhaust gas components. More specifically, the present invention relates to an air-fuel ratio detector for detecting air-fuel ratios over a full operating range of the internal combustion engine of the automobile from a rich range to a lean range.

Air-fuel ratio detectors generally have a structure of a hollow pipe type oxygen sensor as disclosed, for example, in U.S. Pat. No. 4,210,510. Platinum electrodes are disposed on both sides of a zirconia solid electrolyte, and one of the platinum electrodes is exposed to the atmosphere while the other is exposed to the exhaust gas of the engine. This hollow pipe type oxygen sensor detects the air-fuel ratio from the point of sudden change of an electromotive force E (a point generally referred to as a "stoichiometric air-fuel ratio" and at which an air excess ratio $\lambda = 1$), the electromotive force E being generated stepwise by a difference of an oxygen partial pressure in the exhaust gas with the atmosphere being the reference. However, this sensor merely detects whether the air-fuel ratio is greater or smaller than the point $\lambda = 1$, but does not detect the state of the air-fuel ratios which change in a lean range where $\lambda > 1$ and in a rich range where $\lambda < 1$.

Therefore, an air-fuel ratio detector has been developed recently, as disclosed in U.S. Pat. No. 4,292,158, which measures the oxygen concentration in the exhaust gas and detects the air-fuel ratio from the oxygen concentration. In this air-fuel ratio detector, platinum electrodes are disposed on both surfaces of a zirconia solid electrolyte, and a cap having a space diffusion chamber, for example, is fitted to one of the surfaces. A diffusion hole through which the oxygen gas flows is disposed on the cap. This air-fuel ratio detector is exposed as a whole to the exhaust gas, and utilizes an oxygen pump phenomenon using the properties of the zirconia solid electrolyte. When a predetermined voltage is applied across both electrodes of a cell and the change of a pump current $I_P$ is measured, the quantity of this pump current $I_P$ is proportional to the oxygen concentration of the environment. Therefore, the air-fuel ratio $\lambda$ can be detected.

However, this sensor can not detect the stoichiometric air-fuel ratio, though it can detect the air-fuel ratio ($\lambda = 1$) in the lean range ($\lambda > 1$).

Although the inventors of the present invention developed a detector by integrally combining two detection means, it was found that the two detection means interferred with each other and the detection accuracy was low for both the air-fuel ratio in the lean range and the stoicihiometric air-fuel ratio.

SUMMARY OF THE INVENTION

It is therefore an object of the present invention to provide an air-fuel ratio detector which can accurately detect both the lean air-fuel ratio and the stoichiometric air-fuel ratio.

It is another object of the present invention to provide an air-fuel ratio detector which can detect the air-fuel ratios from the lean range to the rich range.

The present invention uses in common one of the electrodes of each of the lean cell and stoichiometric air-fuel ratio cell.

In accordance with the present invention, further, an impressed voltage on the lean cell controls that of the stoichiometric air-fuel ratio cell so as to make it possible to also measure the rich air-fuel ratio.

BRIEF DESCRIPTION OF THE DRAWINGS

FIGS. 9A-9C, 10A-10C, and 11 through 18 show modified examples of the cell of the present invention;

DESCRIPTION OF THE PREFERRED EMBODIMENTS

Figure 1:
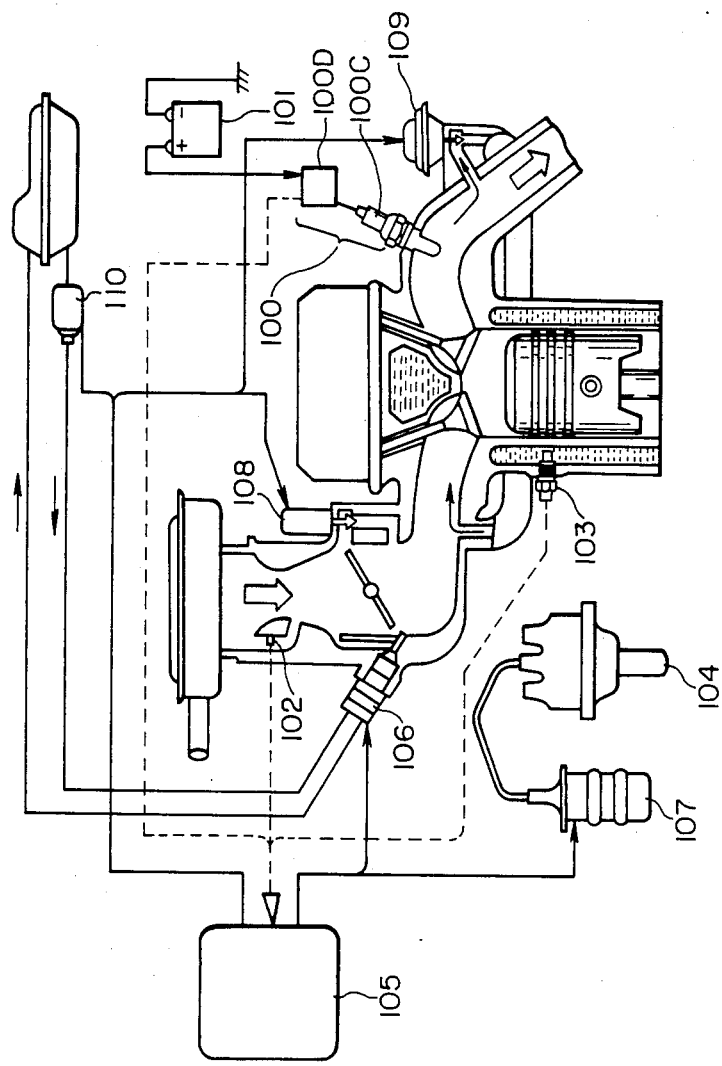
FIG. 1 shows an overall system of an internal combustion engine to which the present invention is applied.

First of all, the construction of an air-fuel ratio controller of an internal combustion engine for use in an air-fuel ratio detector of the present invention will be broadly described with reference to FIG. 1.

The drawing illustrates an example of a system in which engine information from sensors such as an air-fuel ratio detector 100 consisting of an air-fuel ratio cell 100C and a sensor driving circuit 100D, an air flow sensor 102, a water temperature sensor 103, a crank shaft sensor 104, and the like, is supplied to a control unit 105, and is used for controlling a fuel injection valve 106, an ignition coil 107 an idle speed control valve 108, an exhaust gas recirculate control valve 109 and a fuel pump 110. The air-fuel ratio sensor 100 is one of the important devices of this system. A voltage is supplied from a battery 101 to the air-fuel ratio detector 100 to operate it.

Conventional internal combustion engines have been controlled at a stoichiometric air-fuel ratio (air-fuel ratio A/F=14.7, air excess ratio $\lambda = 1$) except when power is required, such as at the time of acceleration. This is because only a stoichiometric air-fuel ratio sensor is available as a practical air-fuel ratio detector and in order to cope with the problem of exhaust gas pollution. It is known that combustion efficiency is maximum with a lean mixture. It is therefore desirable to control the engine for a lean mixture at least in the idle and light load ranges; therefore, a lean sensor capable of detecting with high accuracy the air-fuel ratio in these ranges is important.

Figure 2:
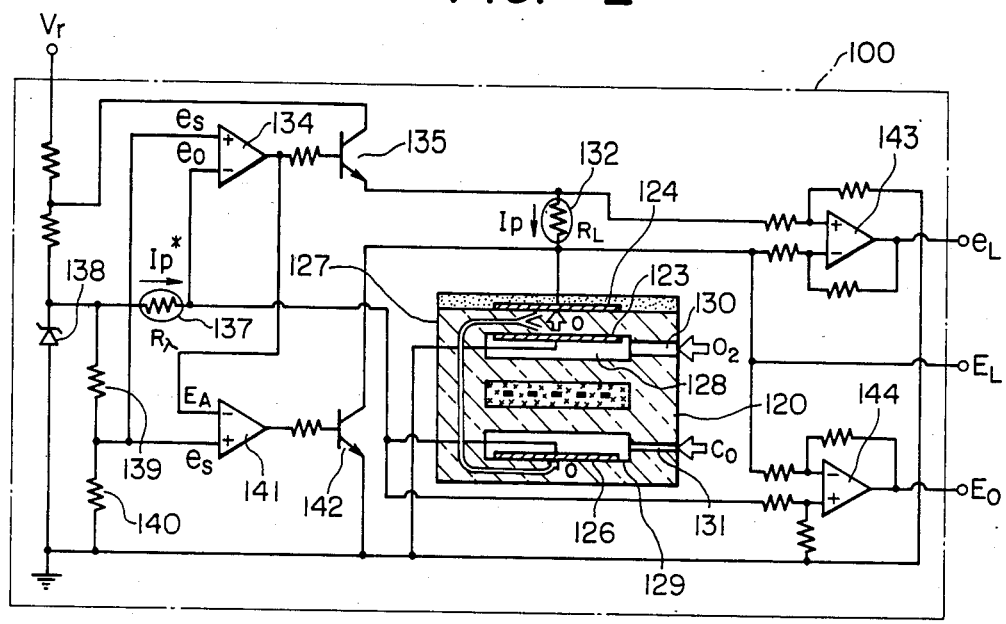
FIGS. 2 through 5 show the construction and explain the operation of one embodiment of the present invention.

An embodiment of the present invention will now be described with reference to FIG. 2.

When the cell is exposed to the exhaust gas, the gas in the exhaust gas flows into diffusion chambers 128, 129 due to diffusion through the diffusion paths 130, 131. When an exciting voltage $E_L$ is applied to the lean cell 127, the oxygen gas that has entered into a diffusion chamber 128 due to diffusion is reduced to oxygen ions (O⁻⁻) at a cathode electrode 123. A set voltage $e_s$ is determined by a zener diode 138 and resistors 139 and 140. The exciting voltage $E_L$ of the lean cell 127 is subjected to feedback control through a first amplifier 134 and a transistor 135 so that the electromotive force $e_o$ of an oxygen reference electrode 126 is equal to the set voltage $e_s$.

The oxygen ions move towards an anode electrode 124 through a zirconia solid electrolyte 120 as indicated by the arrow in the drawing. The oxygen ions are oxidized at the anode portion 124 to change again to oxygen gas, and are emitted into the exhaust gas. The quantity of the oxygen ions which are generated upon application of the exciting voltage $E_L$ to the lean cell 127 and which flow through the zirconia solid electrolyte 120 is measured on the basis of a pumping current value $I_p$ from the voltage detected across a current detecting resistor 132. The pumping current value $I_p$ of the lean cell 127 is called a "limiting current value" in accordance with the rate-determination of diffusion, and is proportional to the oxygen partial pressure (concentration) $P_{o2}$ in the exhaust gas as represented by the following equation:

$$I_p = \frac{4FDS}{RTl} \cdot P_{o2} \qquad (1)$$

where
F: Faraday constant,
D: diffusion constant of oxygen gas,
R: gas constant,
T: absolute temperature,
S: cross-sectional area of diffusion path 130,
l: length of the diffusion path 130.

As described above, the lean function detects linearly the air-fuel ratio of the lean combustion range from the residual oxygen concentration in the exhaust gas.

Next, the stoichiometric function will be described. A current value $I_p^*$ is applied between the oxygen reference electrode 126 and the cathode electrode 123 from a current source (preferably, a constant current source). An exciting current value $I_p^*$ to the oxygen reference electrode 126 is determined by the resistance value $R\lambda$ of an exciting current adjustment resistor 137. A part of the oxygen gas flowing into the diffusion chamber 128 at the diffusion rate-determining speed through the diffusion path 130 is reduced to oxygen ions (O⁻⁻) at the cathode 123, which then moves towards the oxygen reference electrode 126 inside the zirconia solid electrolyte 120, is oxidized to oxygen gas at this reference oxygen electrode 126 and is thereafter emitted into the diffusion chamber 129.

Since the diffusion path 131 is provided so that its resistivity (l/S) is greater by at least ten times than that of the diffusion path 130, the quantity of the gas that flows into the diffusion chamber 129 through the diffusion path 131 is drastically lower than that which flows into chamber 128. As a result, in the rich range, even the quantity of carbon monoxide (CO) which flows due to diffusion into the diffusion chamber 129 through the diffusion path 131 is smaller than the quantity of oxygen which is emitted into the diffusion chamber 129 by the exciting current $I_p^*$ from the current source. Therefore, the oxygen concentration inside the diffusion chamber 129 is above a certain level irrespective of the air excess ratio $\lambda$.

Now, the exciting voltage $E_L$ to the lean cell 127 is subjected to feedback control through the first amplifier 134 and the transistor 135 so that the electromotive force $e_o$ of the oxygen reference electrode 126 is equal to the set voltage $e_s$ (which is selected to be a value of from 0.2 to 1 V, whenever necessary). In other words, since feedback control is effected in such a manner that the oxygen partial pressure ratio between the oxygen reference electrode 126 and the cathode 123 becomes great, the oxygen concentration at the cathode interface portion 123 becomes substantially zero. As a result, the pumping capacity of the cathode 123 is electrically compensated for, the lean cell 127 is less susceptible to the electrode degradation, the formula (1) is strictly reproduced and the reliability of the lean function can be improved. The quantity of the oxygen gas flowing by diffusion into the diffusion chamber 128 through the diffusion path 130 at the stoichiometric air-fuel ratio is stoichiometrically equal to the quantity of the carbon monoxide gas, so that $I_p$ becomes zero at this stoichiometric point. Therefore, the output voltage $E_A$ of the first amplifier 134 and the exciting voltage $E_L$ drops stepwise until they reach zero.

At this time, the difference voltage $\Delta V$ between the oxygen reference electrode 126 and the anode 124 changes stepwise from zero to the order of 1 volt. Therefore, the stoichiometric point can be detected very accurately by utilizing any of those signals ($\Delta V$, $E_A$, $E_L$) which change stepwise. The following description will refer to the case where $\Delta V$ is used for this purpose.

Oxygen and carbon monoxide that flow to the anode electrode 124 through a protective film 125 cause the reaction of the following reaction formula (2) due to the catalytic action of the anode 124 (because it is made of a platinum type material):

$$2CO + O_2 \rightleftarrows 2CO_2 \qquad (2)$$

As a result, the oxygen concentration at the interface of the anode 124 becomes substantially zero at the stoichiometric air-fuel ratio where the quantity of oxygen is stoichiometrically equal to that of carbon monoxide. The oxygen concentration at the interface of the oxygen reference electrode 126 is subjected to the feedback control by an electric circuit so that it exceeds a certain level but does not depend upon the air excess ratio. Therefore, the difference voltage $\Delta V$ changes stepwise at the stoichiometric point. The difference voltage $\Delta V$ can be given as follows where $P_I$ and $P_{II}$ represent the oxygen partial pressures at the interface of the anode 124 and at the interface of the oxygen reference electrode 126, respectively:

$$\Delta V = \frac{RT}{4F} \ln \frac{P_{II}}{P_I} + rI_p^* \qquad (3)$$

The Ohm loss overvoltage $rI_p^*$ of the second item on the right side of the formula (3) can be neglected because the excitation current value $I_p^*$ is sufficiently small, and because the resistance r of the zirconia solid electrolyte 120 is small since the air-fuel ratio sensor is heat-controlled to a constant temperature of at least about 600° C.

The excitation current value $I_p^*$ is sufficiently small when compared with the output current value of the lean cell 127, and does not at all affect the measuring accuracy of the lean function.

This embodiment includes one more improvement. Though the detector as a whole operates without the amplifier 141 and a switch 142, the signal-to-noise ratio (S/N) at the time of detection of the stoichiometric point can be improved by adding these members. In other words, the second amplifier 141 is disposed in order to detect the timing at which the output voltage $E_A$ of the first amplifier 134 is smaller than the set voltage $e_s$, and the output signal of this second amplifier 141 turns on the switch 142 which is connected parallel between the anode 124 and the cathode 123 of the lean cell 127. Though the switch 142 shown consists of a transistor, it may be of an MOS type.

As will be described elsewhere, the output voltage $E_A$ of the first amplifier 134 becomes zero below the excess air ratio $\lambda^*$ on the lean side in the proximity of the stoichiometric point. Therefore, the transistor switch 142 is turned on below the excess air ratio, and the anode 124 and the cathode 123 of the lean cell 127 are electrically connected. When the switch 142 is turned on, the flow of oxygen ions $(O^{--})$ due to the excitation current $I_p^*$ flows towards the oxygen reference electrode 126 also from the anode portion 124 of the lean cell 127. The catalytic action of the anode 124 is improved by this oxygen pump operation, and the reaction of the formula (2) proceeds vigorously. As a result, the oxygen concentration at the interface of the anode 124 becomes extremely small at the air-fuel ratio in the rich range, and the inclination characteristics described already can be improved.

Figure 3:
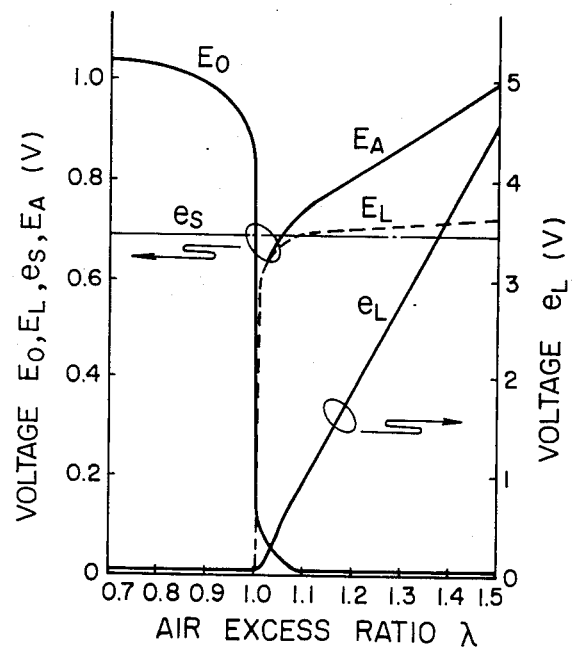

FIG. 3 shows an example of the measurement result of the characteristics of the air-fuel ratio detector having the construction described above. As shown in the diagram, the change width of the signal at the stoichiometric point becomes greater with $E_o$ and $E_L$, and the gentle inclination characteristics in the rich range are found to have been improved. Incidentally, the exciting voltage $E_L$ to the lean cell in the rich range of $\lambda<1$ naturally drops to the zero volt level.

The arrangement in which the oxygen ion flow is directed from the anode portion 124 to the oxygen reference electrode 126 by turning on the switch 142 not only improves the S/N ratio of the stoichiometric function, but also provides the following effect. The oxygen concentration in the exhaust gas atmosphere in the rich range is low. Therefore, in order to supply sufficient oxygen into the diffusion chamber 129 with the excitation current $I_p$, an electrode or electrodes must be additionally disposed as the new oxygen ion supply source(s). In this connection, the anode 124 serves as this new oxygen ion supply source in the rich range of $\lambda<1$. As a result, the drastic drop of the oxygen concentration at the cathode interface portion 123 in the rich range can be prevented, and the zirconia solid electrolyte 120 does not pass into the electron conduction range. This in turn means that the degradation of the endurance of the air-fuel ratio sensor and the reduction of its accuracy become less, and its reliability can be improved. In addition, the output voltage $E_A$ of the first amplifier 134 can be used as the output signal of the stoichiometric sensor.

Since the exciting voltage $E_L$ of the lean cell 127 is subjected to feedback control, the response of the lean cell can be improved dramatically. This effect will be explained in further detail with reference to FIGS. 4 through 8.

Figure 4:
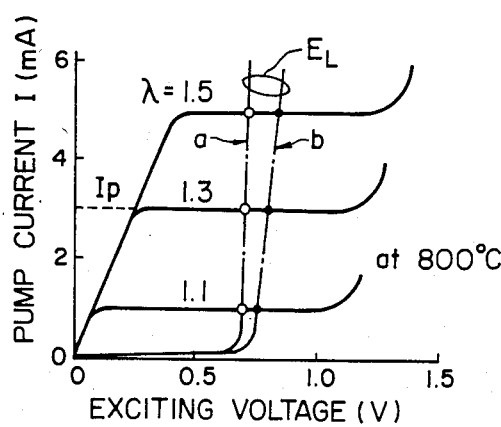

FIG. 4 shows the V-I characteristics of the lean cell 127. The diagram shows the characteristics of the current which is pumped inside the zirconia solid electrolyte by the excitation voltage E. As the exciting voltage E becomes greater, the pump current value I increases gradually until it reaches saturation at a constant value. This saturation current value $I_p$ is the critical current value determined by the aforementioned formula (1). As the excitation voltage E is further increased, the zirconia solid electrolyte exhibits electron conductivity, and the current value I increases abruptly. In the case of the lean sensor, therefore, this saturation current value $I_p$ must be detected, and the exciting voltage $E_L$ at the time of driving the lean cell is set to a suitable value by referring to this diagram. In the case of the circuit construction shown in FIG. 2, the excitation voltage $E_L$ of the lean cell 127 does not depend upon the air excess ratio (provided that within the range of $\lambda>1$), but is set to a substantially constant level as represented by a characteristics curve a. When the excitation voltage $E_L$ is gradually increased in response to the excess air ratio $\lambda$ as represented by a characteristics curve b, the response of the lean sensor is confirmed experimentally to have been improved remarkably.

Figure 5:
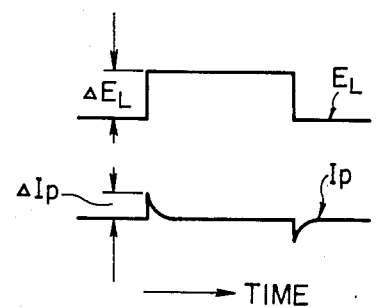

This phenomenon will be explained with reference to FIG. 5. When the excitation voltage $E_L$ is changed stepwise within such a range in which no change occurs in the air excess ratio of the air-fuel ratio sensor atmosphere but in which the pump current value I exhibits the saturation current value (the critical current value), the characteristics of $E_L$ like the differential waveform are added to the output current value $I_p$. The present invention intends to utilize this phenomenon to improve the response of the lean sensor. Experiments reveal that the change width $\Delta I_p$ of the output current value $I_p$ depends substantially upon the change width $\Delta E_L$ of the exciting voltage $E_L$.

Figure 6:
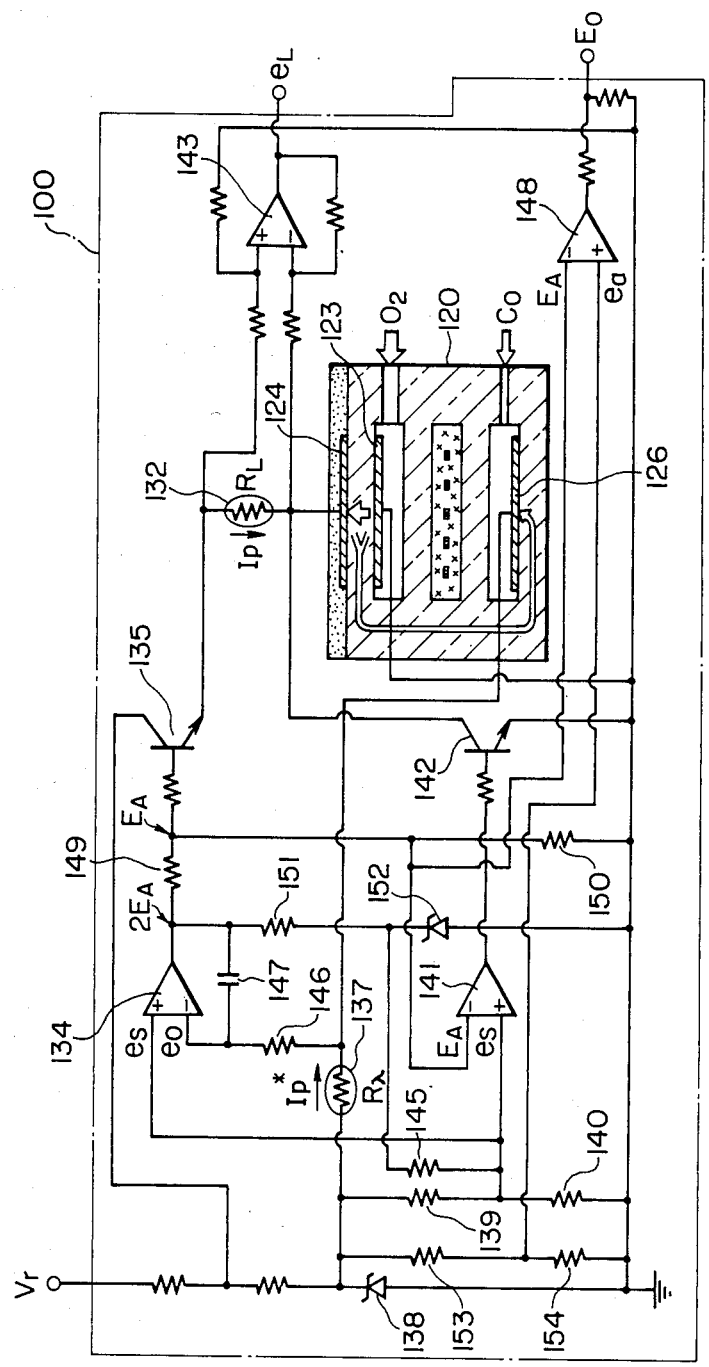

FIG. 6 shows the overall construction of the air-fuel ratio detector for an automobile in accordance with another embodiment of the present invention. This embodiment is characterized in that the output voltage $E_A$ of the first amplifier 134 is positively fed back to the decision portion of the set voltage $e_s$ through a resistor 145. An integration circuit consisting of a resistor 146 and a capacitor 147 is disposed in order to prevent a transient oscillation phenomenon that occurs in the output signal $e_L$ of the lean sensor due to the aforementioned positive feedback circuit.

In the air-fuel ratio detector shown in FIG. 6, the set voltage $e_s$ is variable from 0.75 V to 0.80 V in response to the excess air ratio $\lambda$ on the lean side. As a result, the excitation voltage $E_L$ of the lean cell 127 is automatically subjected to feedback control to a large value in accordance with the air excess ratio $\lambda$ as represented by the characteristics curve b in FIG. 4. Even if the excitation voltage $E_L$ of the lean cell 127 is made variable, the output signal $e_L$ of the lean sensor, the signal $E_o$ that can be used as the output signal of the stoichiometric sensor and the voltage $E_L$ exhibit good characteristics with only slight hysteresis.

Figure 7:
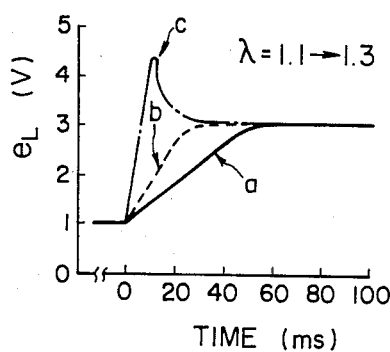
FIGS. 6 through 8 show the construction and explain the operation of another embodiment of the present invention.

FIG. 7 shows an example of the actual measurement result of the response improving effect of the lean sensor output signal when the set voltage $e_s$ is made variable (that is, the excitation voltage $E_L$ for a lean mixture is made variable) for a lean mixture. The diagram shows the mode of change of the output signal $e_L$ of the lean sensor as the output voltage of a differential amplifier 143 when the excess air ratio is changed stepwise from 1.1 to 1.3. The diagram shows the case where the characteristics a do not depend upon the excess air ratio and the exciting voltage $E_L$ of the lean cell 127 is kept constant.

The characteristics b represent the case where the exciting voltage $E_L$ is made suitably variable in accordance with the excess air ratio λ. It is found that its response can be reduced to about half of that of the characteristics a. As a result, the time constant τ of the lean sensor, which is as small as about 16 ms, can discriminate the air-fuel ratio for each cylinder and can control the unstable air-fuel ratios. When the change width of the exciting voltage $E_L$ with respect to the air excess ratio λ is increased, the transient characteristics cause undesirable over-shoot as indicated by c characteristics.

Figure 8:
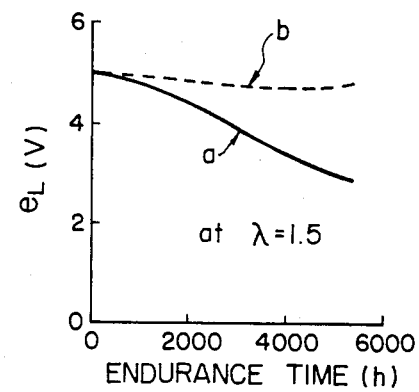

Next, FIG. 8 shows an example of the actual measurement result of the endurance of the lean sensor. Characteristics a represent the change with time of a lean cell single body, and it is found that its output signal drops gradually with the drop of the pumping capacity of the cathode 123. However, the construction of the present invention in which the exciting voltage $E_L$ of the lean cell 127 is subjected to feedback control so that the electromotive force $e_o$ of the oxygen reference electrode 126 is equal to the set voltage $e_s$, operates in such a manner as to compensate for the drop of the pumping capacity of the cathode 123 with the passage of time. As a result, the change of the output signal of the lean sensor in accordance with the present invention becomes smaller as represented by the b characteristics, and the endurance can be remarkably improved.

Next, measures for improving the endurance of the stoichiometric function and the yield will be described.

A suitable exciting current value $I_p^*$ must be set in order to obtain a suitable stoichiometric function which has less hysteresis and is free from a level drop in the rich range. This object can be accomplished by incrementally changing the set voltage $e_s$ at the stoichiometric point in such a manner as to set it to a low level for a rich mixture and to a high level for a lean mixture. In other words, as will be described elsewhere, a satisfactory stoichiometric function can be obtained even when the exciting current value $I_p^*$ is as small as 0.05 mA. In order for the lean cell 127 to highly accurately detect the critical current value $I_p$, the exciting voltage $E_L$ must be made at a level exceeding a certain level, and the set voltage $e_s$ on the lean side can not be set to too small a value. From the aspect of the endurance of the stoichiometric function, too, it is advantageous to change in a stepwise manner the set voltage $e_s$ at the stoichiometric point. In other words, if the catalytic action of the anode 124 deteriorates with the passage of time or if microfissures occur in the diffusion chamber 129, it is expected that the electromotive force for the rich mixture will be reduced.

FIG. 6 shows one example of the construction which changes stepwise the set voltage $e_s$ at the stoichiometric point. The output voltage of the first amplifier 134 is made to be $2E_A$ by adding new resistors 149 and 150 that have not been explained previously. This point is connected to the ground point via a resistor 151 and a zener diode 152 (for 3 V in the drawing). The change width of the set voltage $e_s$ in the lean range is limited by positively feeding back the voltage across the resistor 151 and the zener diode 152 to the set voltage $e_s$ determination portion, and the change width at the stoichiometric point can thus be increased.

A comparator 148 generates a switching-like stoichiometric signal e. That is, when the voltage $E_A$ becomes smaller than a slice level which is determined by resistors 153 and 154, it generates an H (high) level voltage signal $e_{80}$.

Next, various embodiments having a tri-electrode structure will be explained with reference to FIGS. 21 through 30.

FIGS. 9(b) and 9(c) are sectional views taken along lines A—A and B—B of FIG. 9(a), respectively. In FIG. 9, a heater 122 encompassed by an insulating member 121 such as alumina is disposed at the center of the zirconia solid electrolyte 120, and the zirconia solid electrolyte 120 is equipped at its upper portion with the cathode 123, the anode 124 and a porous protective film 125, whereas it is equipped at its lower portion with the oxygen reference electrode 126. The portion consisting of the zirconia solid electrolyte 120, the cathode 123 and the anode 124 represents a lean function cell as will be described later, and this portion will be hereinafter called a "lean cell 127".

The cathode 123 and the oxygen reference electrode 126 are disposed inside diffusion chambers 128 and 129, respectively, and come into contact with an exhaust gas as the object atmosphere to be measured, through slit-like diffusion paths 130 and 131, respectively. Preferably, the diffusion path 130 serving as a gas diffusion resistor is produced so that its resistivity is greater by at least some dozens of multiples than that of the diffusion path (on the communication side with the oxygen reference electrode 126) 131. In other words, it is produced in such a fashion that the gas can not easily flow from the exhaust gas atmosphere into the diffusion chamber 129. As will be described later, the present invention is based upon the principle that the stoichiometric air-fuel ratio is detected by controlling the oxygen concentration at the oxygen reference electrode 126 by the oxygen pump action. Therefore, an introduction path of a reference atmosphere is not necessary, and the structure of the sensor does not become complicated. All of the three electrodes (the cathode 123, the anode 124 and the oxygen reference electrode 126) can be made of a high melting point material having a high durability, such as of a platinum type without using non-catalytic gold electrodes.

As a result, it becomes possible to laminate the overall structure of the sensor portion shown in the drawing by thick film process techniques, and to sinter it simultaneously and integrally at a high temperature of about 1,500° C. In this case, the diffusion paths and the diffusion chambers can be simultaneously formed with the integral sintering by a baking method of a carbon type organic binder. Since no air introduction path exists, the zirconia solid electrolyte 120 can be directly heated by the heater 122 so that the heat efficiency of the heater 122 can be improved. In this case, the laminate member of the sensor portion has a vertically symmetric structure with respect to the heater 122, provides excellent temperature distribution for the sensor portion and can control the temperature at a high constant temperature so that an air-fuel ratio detector having high accuracy but less temperature influence can be obtained.

Still another embodiment is shown in FIG. 10. In the embodiment shown in FIG. 10, the slit-like diffusion paths 130 and 131 in FIG. 9 are changed to those which are of a bored hole type.

There is no theoretical problem even if these diffusion paths 130 and 131 are made of a high porous material.

In the embodiments shown in FIGS. 9 and 10, the extreme right portion of the sensor portion is omitted, but this extreme right portion is fixed to a plug member having a suitable shape, and is fitted to an exhaust pipe through this plug member.

Other embodiments of the invention are shown in FIGS. 11 through 18.

Figure 11:
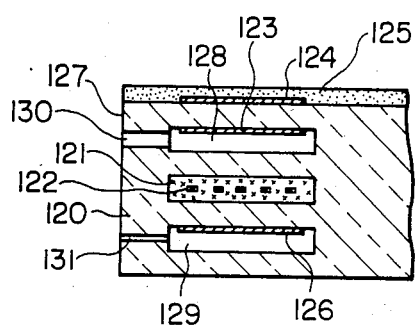

The embodiment shown in FIG. 11 is characterized in that the oxygen reference electrode 126 is disposed at an upper portion of the diffusion chamber 129. The diffusion paths 130 and 131 are shown schematically, as described above.

Figure 12:
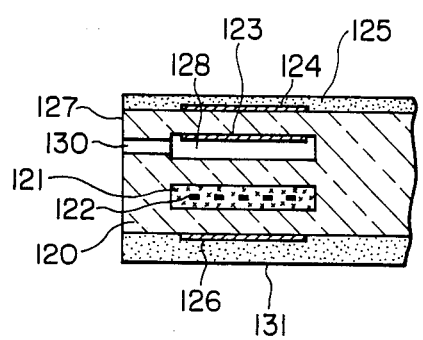

The embodiment shown in FIG. 12 has a construction in which the diffusion path 131 of FIG. 11 is made of a porous member. In this case, the porous member is by far thicker than the protective film 125, or is made of a material having a low porosity.

Figure 13:
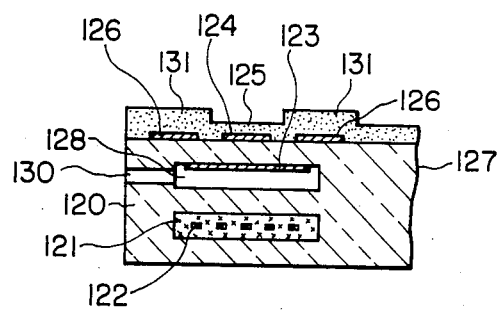

The embodiment shown in FIG. 13 has a construction in which the diffusion path 131 of FIG. 12 is disposed on the side of the lean cell 127. Though two oxygen reference electrodes 126 may seen to exist in the drawing, it is connected plane-wise, and it is to be noted that the air-fuel ratio detector has also a tri-electrode structure.

Figure 14:
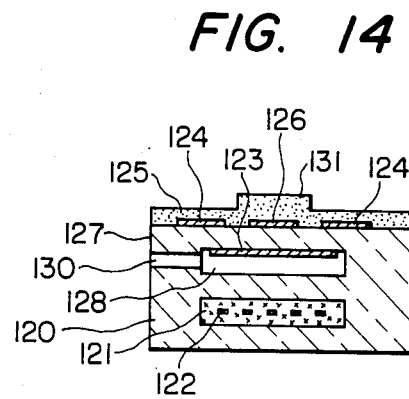

The embodiment shown in FIG. 14 has a construction in which the relative disposition of the protective film 125 and the diffusion path 131 in FIG. 13 is reversed.

Figure 15:
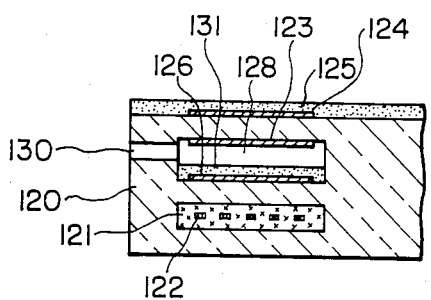

The embodiment shown in FIG. 15 has a construction in which the oxygen reference electrode 126 is disposed in the diffusion chamber 128 via a porous diffusion path 131.

Figure 16:
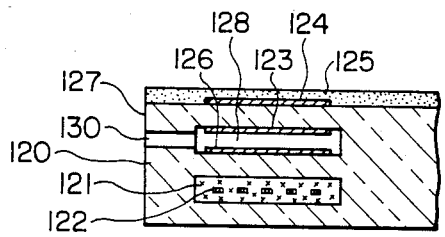

The embodiment shown in FIG. 16 has a construction in which the diffusion path 131 of FIG. 15 does not exist. Though accuracy is reduced, the detector theoretically has the function of a composite sensor.

Figure 17:
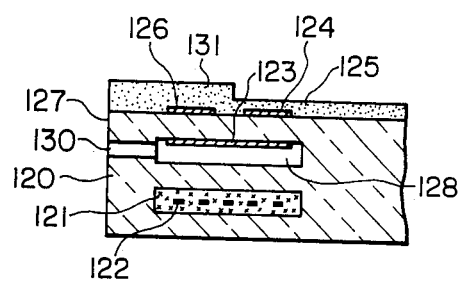

FIG. 17 shows an embodiment which as an intermediate arrangement between FIGS. 13 and 14.

Figure 18:
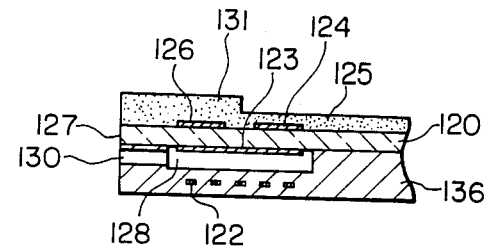

FIG. 18 shows the embodiment in which an insulating member 121 consists of a substrate-like insulating member such as an alumina substrate.

The embodiments described above provide an air-fuel ratio detector having a tri-electrode structure formed on the same zirconia solid electrolyte and incorporating therein a heater. These embodiments provide the following effects in accordance with the direction of the oxygen ion stream between the electrodes, the driving method of the switch disposed in parallel with the lean cell, and the controlling and setting method of the feedback of the electromotive force of the oxygen reference electrode.

(1) The structure of the air-fuel ratio detector and the structure of its driving circuit become simple.

(2) The accuracy and reliability of the air-fuel ratio detector can be improved.

(3) The response of the air-fuel ratio detector can be improved.

(4) Thick film through-process and the simultaneous and integral sintering process of the sensor portion become possible, and the mass-producibility of the air-fuel ratio detector can be improved.

(5) The adjustment method of the air-fuel ratio detector becomes simple, and the production yield can be improved.

Next, still another embodiment of the present invention will be described with reference to FIG. 19.

In the drawing, the zirconia solid electrolyte 1 has a sectional shape such as shown in the drawing, and forms three layers 1A, 1B and 1C. A pair of platinum electrodes 2 and 3 are disposed in such a manner as to interpose the layer 1A between them. Another platinum electrode 6 is disposed on the layer 1C. The layers 1A and 1B together form a diffusion chamber 8, while the layers 1B and 1C together form a diffusion chamber 9. A gas diffusion hole 10 is formed in the diffusion chamber 8, while a gas diffusion hole 11 is disposed in the diffusion chamber 9. In the drawing, the layer 1A of the zirconia solid electrolyte 1 and the platinum electrodes 6, 2 together constitute a stoichiometric air-fuel ratio detection cell. In this embodiment, both cells are integrated and are as a whole exposed to the exhaust gas.

Next, the operation of this embodiment will be described. Before the definite operation of the embodiment shown in FIG. 19 is described in detail, the fundamental operation will be first explained with reference to FIG. 20 showing the principal portions. Here, a fourth electrode 7 is added for the sake of explanation.

Figure 21:
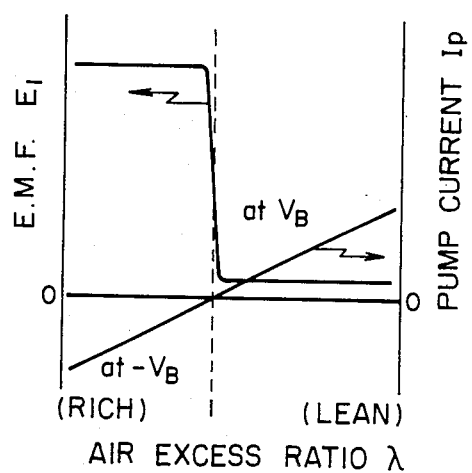

First of all, the operation of the air-fuel ratio detection cell in the lean range will be described. In the lean range of the air-fuel ratio detection cell, a voltage $V_B$ (e.g., 0.5 V) is applied from the exciting voltage source 12 across the platinum electrode 3 as the anode and the platinum electrode 2 as the cathode, and the oxygen existing inside the diffusion chamber 8 is then reduced to oxygen ions by the platinum electrode 2. The oxygen ions pass through the layer 1A of the zirconia solid electrolyte 1 and move towards the anode (the platinum electrode 3). The ionized oxygen is oxidized by the platinum electrode 3 and is changed again to oxygen, and is thereafter emitted into the exhaust gas from the side of the platinum electrode 3. The oxygen in the exhaust gas flows into the diffusion chamber 8 through the gas diffusion hole 10. The pumping current $I_p$ (the critical current) obtained when the quantity of oxygen emitted from the platinum electrode 3 into the exhaust gas balances with the quantity of oxygen flowing into the diffusion chamber 8 through the gas diffusion hole 10 is proportional to the oxygen concentration as shown in FIG. 21. Therefore, the oxygen concentration in the exhaust gas can be detected by measuring this pumping current $I_p$.

Next, the operation of the air-fuel ratio detection cell in the rich range will be described.

The quantity of oxygen in the exhaust gas in the rich range is only limited, but carbon monoxide (CO) increases in the rich range, that is, with the smaller air excess ratio λ. Therefore, the following reaction takes place between CO and $O_2$ inside the diffusion chamber 8.

$$CO + \tfrac{1}{2}O_2 \rightleftharpoons CO_2 \qquad (4)$$

From the relation of the formula (4), oxygen is supplied into the diffusion chamber 8 in the rich range in contrast to the lean range so that it reacts with CO coming into the diffusion chamber 8, and the pumping current $I_p$ changes in accordance with the quantity of CO. Therefore, the CO quantity can be detected from the value of this pumping current $I_p$, and the air excess ratio λ can be detected as shown in FIG. 21.

The above can be accomplished by reversing the polarity of the voltage to be applied to the platinum electrodes 2 and 3 in the lean range, that is, by using the platinum electrode 2 as the anode and the platinum electrode 3 as the cathode, and applying the voltage $V_B$ from the exciting voltage source 12.

In the stoichiometric air-fuel ratio detection cell, the platinum electrode 6 is used as the anode and the platinum electrode 2 is used as the cathode, throughout the full air-fuel ratio ranges, and a constant current $I_{PC}$ is caused to flow so that oxygen is supplied into the diffusion chamber 9. Since the diffusion hole 11 is smaller than the diffusion hole 10, the diffusion chamber 9 is filled with oxygen and enters a state equivalent to the atmosphere. Therefore, the ratio $d_1/d_2$ of the area $d_1$ of the diffusion hole 10 of the air-fuel ratio detection cell to the area $d_2$ of the diffusion hole 11 of the stoichiometric air-fuel ratio detection cell must satisfy the following relation:

$$d_1/d_2 \geq 10/1 \qquad (5)$$

As a result, an electromotive force $E_1$ of about 1 V is generated between both electrodes at the point of the stoichiometric air-fuel ratio $\lambda = 1$, as is known from Nernst's equation. Therefore, the stoichiometric air-fuel ratio point $\lambda = 1$ can be detected by detecting the point of occurrence of this electromotive force $E_1$, as can be seen from FIG. 21.

It can be understood from the above that in order to detect the air-fuel ratio in all operating ranges, a positive excitation voltage $V_{B1}$ (e.g., 0.5 V) is applied in the lean range and negative excitation voltage $-V_{B2}$ (e.g., $-0.5$ V) is applied in the rich range to obtain the pumping current $I_P$ which corresponds to the air excess ratio $\lambda$. Here, the timing of the inversion of polarities of the excitation voltages $V_{B1}$ and $V_{B2}$ can be decided by using the electromotive force $E_1$ generated by the stoichiometric air-fuel ratio detection cell as a switching timing signal.

Turning back again to FIG. 19, this embodiment will now be described.

In the drawing, $V_r$ is a reference voltage source such as a car battery 101; 20 and 21 are resistors connected to the reference voltage source; $T_R$ is an npn transistor whose collector is connected to the junction of the resistors 20 and 21 and whose emitter is grounded; $A_1$ is an operational amplifier whose (+) input terminal is connected to the collector of the transistor $T_R$ and whose output terminal is connected to a negative input terminal; 23 is a pumping current detection resistor which is connected to the output terminal of the operational amplifier $A_1$; $C_1$ is a comparator whose (+) input terminal is connected to the output E of a platinum electrode 6 and whose (−) input terminal is connected to a threshold voltage $V_{th}$ (e.g., 1 V); 24 through 29 are resistors; $A_2$ is another operational amplifier whose (+) input terminal is connected to the junction of the resistors 24, 25 and 26 and whose (−) input terminal is connected to the junction of the resistors 27, 28 and 29; $V_b$ is a bias voltage source as a reference of the level of an exciting voltage driving the cell; $V_{IP}$ is an output; 30 is a resistor; 31 is a zener diode for obtaining the reference voltage; 32 is a resistor for obtaining a constant current $I_{PC}$ from the constant voltage of the zener diode 31; and 33 and 34 are resistors for dividing the constant voltage of the zener diode 31. The resistors 20, 21, 30, 32, 33, 34 and the zener diode 31 constitute a power source circuit 35 for forming the voltage and current as the reference. The resistors 24, 25, 26, 27, 28, 29 and the operational amplifier $A_2$ constitute an addition/subtraction circuit 36 for processing the output signals. The comparator $C_1$ and the transistor $T_R$ constitute a voltage control circuit.

The wide range air-fuel ratio detector of this embodiment is constructed as described above.

Next, the operation of the embodiment shown in FIG. 19 will be described.

To detect the air-fuel ratios in all operating ranges as described above, the polarity of the exciting voltage of the air-fuel ratio detection cell must be changed to $V_{B1}$ or $-V_{B2}$ at the point of the stoichiometric air-fuel ratio ($\lambda = 1$). Therefore, three power sources including a ground level are necessary for the exciting voltage of the air-fuel ratio cell. However, since a car uses a unipolarity battery as a power source, voltages of both polarities are obtained by a reference bias method of the exciting voltage. This can be accomplished by the reference voltage $V_r$, the resistors 20 and 21, the transistor $T_R$, the bias voltage source $V_b$ and the comparator $C_1$. In other words, when the output E of the stoichiometric air-fuel ratio cell is smaller than the threshold voltage $V_{th}$ in the lean range, the output of the comparator $C_1$ is at the low level, and the transistor $T_R$ is cut off. When the cell output E is greater than the voltage $V_{th}$ in the rich range, the output of the comparator $C_1$ is at the high level and the transistor $T_R$ is turned on.

Therefore, besides the bias voltage source $V_b$, the voltage is $V_{B1}'$ when the transistor $T_R$ is cut off and is at the ground level when the transistor $T_R$ is turned on, and the three voltage sources have the relation below:

$$V_{B1}' > V_b > 0$$

Here, $V_{B1}'$ and $V_b$ are selected to be 1 V and 0.5 V, respectively, by way of example. Accordingly, the output of the operational amplifier $A_1$ is $V_{B1}'$ in the lean range, and the current flows from $V_{B1}'$ to $V_b$ with the platinum electrode 3 being at a high potential. Needless to say, the exciting voltage between both electrodes in this case is $V_{B1} = V_{B1}' - V_b$ (with the proviso that the voltage drop of the resistor 23 is small and can be neglected). In the rich range, the platinum electrode 3 is at the ground level, and the current flows from $V_b$ (corresponding to $-V_{B2}$ described above) with the platinum electrode 2 being at the high potential. Thus, the supply or withdrawal of oxygen into and from the diffusion chamber 8 is effected.

To bring the output of the operational amplifier $A_1$ to $V_{B1}'$ in the lean range and to the ground level in the rich range, the comparator $C_1$ compares whether or not the electromotive force E (0.6 V ~ 1.4 V) of the stoichiometric air-fuel ratio cell is greater than the threshold voltage $V_{th}$ (here, 1 V), and when the former is greater than the latter, the present operating state is judged as "rich" and when the former is smaller, the operating state is judged as "lean", thereby effecting ON-OFF control of the transistor $T_R$.

The pumping current $I_p$ flowing through the air-fuel ratio cell in accordance with the air-fuel ratios in the lean and rich ranges is detected from the potential difference at both ends of the pumping current detection resistor 23. The addition/subtraction circuit 36 consisting of the resistors 24~29 and the operational amplifier $A_2$ processes the output signals.

The output $V_{IP}$ of the operational amplifier $A_2$ is given by the following equation with $e_{24}$, $e_{25}$, $e_{27}$ and $e_{28}$ being the voltages applied to the resistors 24, 25, 27 and 28, respectively:

$$V_{IP} = (e_{24} + e_{25} - e_{27} - e_{28}) \cdot K \qquad (6)$$

Here, K is the gain of the operational amplifier $A_2$, and is 1 (K=1) when the resistors 24 through 29 have the same resistance value. Since the input voltage $e_{28}$ is at the ground level, it is 0 (zero), and the equation (6) becomes as follows:

$$V_{IP} = e_{24} + e_{25} - e_{27} \tag{7}$$

Therefore, the output $V_{IP}$ in the full air-fuel ratio ranges is a value obtained by adding a potential difference $\Delta V_{IP}$ at the resistor 23 due to the pumping current to the $V_b$ reference value in the lean range, and is a value obtained by subtracting $\Delta V_{IP}$ from $V_b$ in the rich range. In this manner, an air-fuel ratio sensor for a car which can obtain an analog and continuous output $V_{IP}$ in the full air-fuel ratio range can be accomplished.

Figure 22:
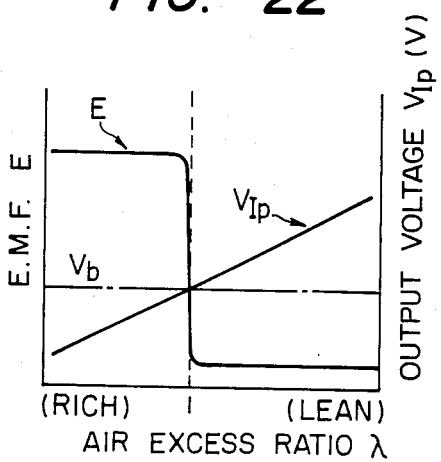

FIG. 22 shows the characteristics of the air-fuel ratio detector. As a result, the output voltage $V_{IP}$ can be obtained as a linear and analog quantity in the full air-fuel ratio range, that is, at all the air excess ratios $\lambda$.

Figure 23:
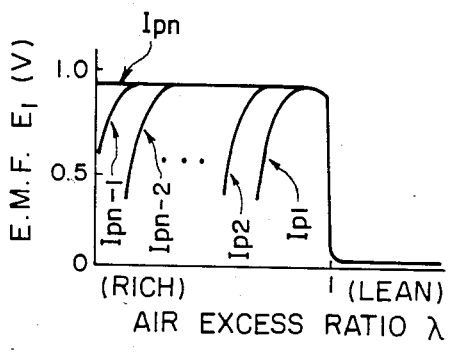
FIGS. 23 through 28 show the construction and explain the operation of still another embodiment of the present invention.

Next, a supplementary explanation will be given relating to the stoichiometric air-fuel ratio sensor shown in FIG. 19 before other embodiments of the present invention are described. This sensor consists of the solid electrolyte 1C, the platinum electrodes 6 and 7, the diffusion chamber 9 and the diffusion hole 11. The sensor is as a whole exposed to the exhaust gas. The inside of the diffusion chamber 9 is controlled to a high oxygen concentration by causing the constant current $I_{PC}$ to flow throughout the full air-fuel ratio range, and the point at which the air excess ratio $\lambda$ is 1 is detected from the electromotive force E. However, since carbon monoxide CO increases in the rich range, if the quantity of oxygen to be transferred into the diffusion chamber (which corresponds to the quantity of the constant current $I_{PC}$) is insufficient, the output of the electromotive force $E_1$ will drop due to the reaction of oxygen with carbon monoxide CO expressed by the reaction formula (4). The characteristics shown in FIG. 23 represent the relation between the constant current $I_P$ and the electromotive force $E_1$. As shown in this drawing, $I_P$ must be increased with decreasing $\lambda$ in order to prevent the output drop of the electromotive force $E_1$ in the rich range.

Therefore, if the current to be passed is variably controlled throughout the rich range so that the electromotive force $E_1$ of the stoichiometric air-fuel ratio cell becomes constant, a variable current $I_C$ corresponding to each $\lambda$ can be obtained, and their relation is proportional.

Figure 25:
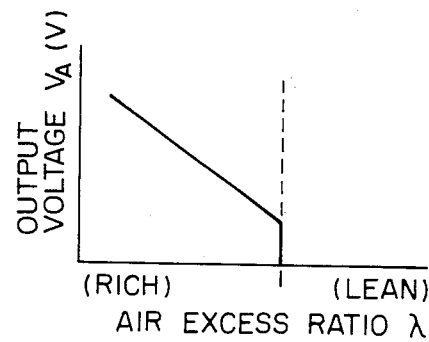
Figure 24:
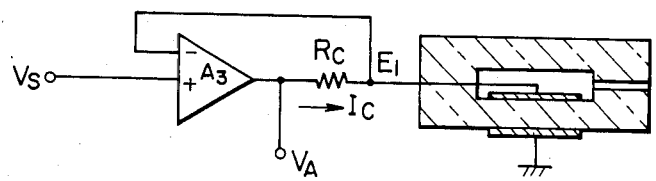

FIG. 24 shows a definite circuit for realizing the above. In the drawing, if a set voltage $V_s$ (e.g. 0.9 V) equal to the electromotive force $E_1$ to be controlled is set to the operational amplifier $A_3$, control is made in such a fashion that the positive input terminal voltage is equal to the negative input terminal voltage from the condition for the stable operation of the operational amplifier. Therefore, the electromotive force $E_1$ of the stoichiometric air-fuel ratio cell is equal to $V_s$. For this reason, the air-fuel ratio in the rich range $\lambda = 1$ including the point of the stoichiometric air-fuel ratio can be detected from the variable current $I_C$ flowing through the resistor $R_C$ or from the difference voltage across both ends of $R_C$ or from the change quantity of the output voltage $V_A$ of the operational amplifier $A_3$ with respect to $\lambda$. FIG. 25 shows such characteristics. The output $V_A$ of the operational amplifier $A_3$ is inversely proportional to $\lambda$ plotted on the abscissa. The offset voltage of the output $V_A$, which appears as the point of $\lambda = 1$, can be easily eliminated by signal processing, and $\lambda = 1$ can also be detected by positively utilizing the signal processing.

The method described above in combination with the driving method in the lean range of this embodiment can realize an air-fuel ratio detector having a wide detection range.

Sensors utilizing the oxygen pump phenomenon are used at high temperatures with the lower limit being at about 600° C. Therefore, these sensors need a heater, and an electrode and lead wires must be increased accordingly. If the electrode is eliminated, it is advantageous for both the production process and the production cost.

Other embodiments of the invention to accomplish the above-mentioned two points will be described with reference to FIG. 26.

The air-fuel ratio detection cell consists of the zirconia solid electrolyte 50 and the platinum electrodes 51, 52, while the stoichiometric air-fuel ratio detection cell consists of the zirconia solid electrode 50 and the platinum electrodes 53, 51. The operation of the former is already described. The high oxygen concentration control in the stoichiometric air-fuel ratio cell is made by applying a current to the platinum electrode 53 as the anode and the platinum electrode 51 as the cathode.

In the drawing, $V_{B1}'$ is a lean control set voltage; $V_{s2}$ is a rich control set voltage; $A_4$ and $A_5$ are operational amplifiers whereby $A_4$ is for driving the air-fuel ratio cell and $A_5$ for the stoichiometric air-fuel ratio detection cell; $R_L$ is a pump current detection resistor; $R_F$ is a resistor for detecting a variable current $I_C$; $C_2$ is a comparator for comparing the electromotive force of the stoichiometric air-fuel ratio detection cell with $V_{s1}$; SW is a switch which is controlled by the comparator $C_1$; $e_L$ is a lean output voltage; and $e_R$ is a rich output voltage.

Figure 19:
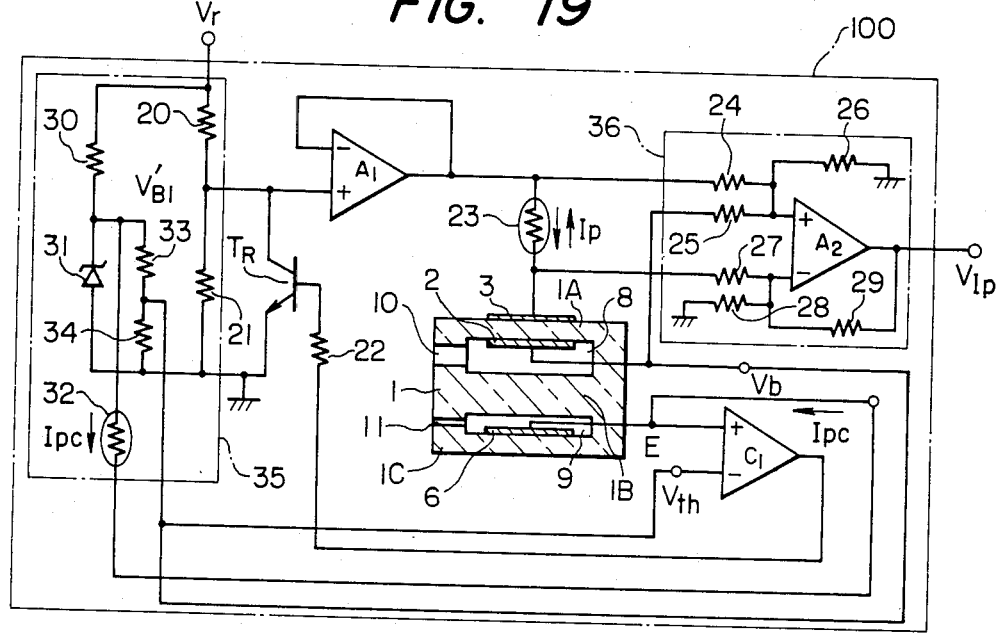
FIGS. 19 through 22 show the construction and explain the operation of still another embodiment of the present invention.
Figure 20:
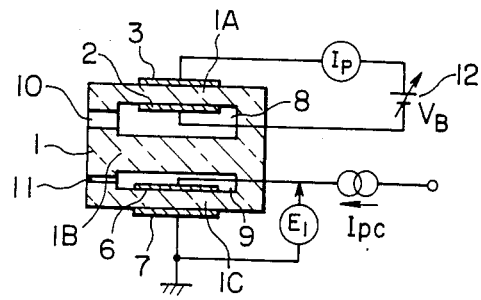

The construction of the addition/subtraction circuit 36 is the same as that shown in FIG. 19. The rich output voltage $e_R$ is applied to the (−) input terminal of the operational amplifier $A_2$. The power source circuit 37 is fundamentally the same as that shown in FIG. 2.

When both cells of the tri-electrode structure are simultaneously driven, most of the oxygen at the interface of the platinum electrode 51 in the air-fuel ratio detection cell is transferred to the platinum electrode 52, but oxygen, though in a limited quantity, is also transferred to the platinum electrode 53 side (diffusion chamber) of the stoichiometric air-fuel ratio detection cell, thereby causing mutual interference, and exterting adverse influences upon the measuring accuracy of the former cell. The interferrence between both cells can be prevented on the driving circuit side by controlling the air-fuel ratio detecting cell so that the electromotive force of the stoichiometric air-fuel ratio detection cell (the terminal voltage $E_o$ of the platinum electrode 53) becomes a certain constant voltage $E_o$ (by making the quantity of oxygen at the interface of the platinum electrode 51 zero). In this case, the control value of the terminal voltage $E_o$ is selected from the range of from 0.2 V to 1 V (0.5 V in this embodiment).

The lean control set voltage $V_{B1}'$ is applied to the operational amplifier $A_4$ corresponds to $E_o$ in the lean range, and controls the terminal voltage of the stoichiometric air-fuel ratio detection cell to $V_{B1}'$. The oxygen concentration in the atmosphere, that is, the air-fuel ratio, can be detected at this time by detecting the pumping current $I_P$ flowing through the resistor $R_L$. Therefore, the lean output voltage $e_L$ is produced by the pumping current $I_P$ and the voltage drop due to the pumping current detection resistor $R_L$. In the range where the operating condition is $\lambda=1$, the electromotive force is produced stepwise, so that the input terminal of the (−) terminal of the operational amplifier $A_4$ becomes greater than $V_{s1}$, and the output of $A_4$ becomes zero.

On the other hand, the rich control set voltage $V_{s2}$ applied to the operational amplifier $A_5$ corresponds to $E_o$ in the rich range, and controls the terminal voltage $E_o$ in the range of $\lambda=1$ by the operational amplifier $A_5$ so that $E_o$ becomes $V_{s2}$. The operation here is already described with reference to FIG. 24, and the feed current $I_C$ is variably controlled so that the terminal voltage $E_o$ which drops due to the CO diffusion into the diffusion chamber becomes $V_{s2}$. In this manner, the output of the stoichiometric air-fuel ratio detection cell, that is, the rich output voltage $e_R$, can be obtained from the output voltage of the operational amplifier $A_5$ which changes in response to $\lambda$ as shown in FIG. 25.

The comparator $C_2$ and the switch SW are disposed in order to process signals in the lean range of the rich output voltage $e_R$. In the lean range, the input relation of $A_5$ is $V_{s2}>V_{s1}$ ($E_o$) and the output is generated. Therefore, in this range, the switch SW is turned off by the comparator $C_2$ so as to remove the rich output voltage $e_R$. In the rich range, the switch SW is turned on, on the contrary, so as to produce the rich output voltage $e_R$.

Figure 27:
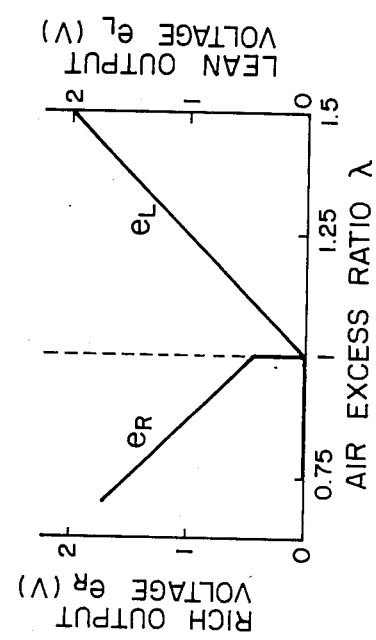

FIG. 27 shows an example of the characteristics of an experiment conducted by the method described above. The abscissa represents the excess air ratio $\lambda$, and the ordinate represents the rich/lean output voltages $e_R$, $e_L$. A linear lean output voltage $e_L$ can be obtained when $\lambda>1$ and a linear rich output voltage $e_R$, when $\lambda<1$.

Figure 28:
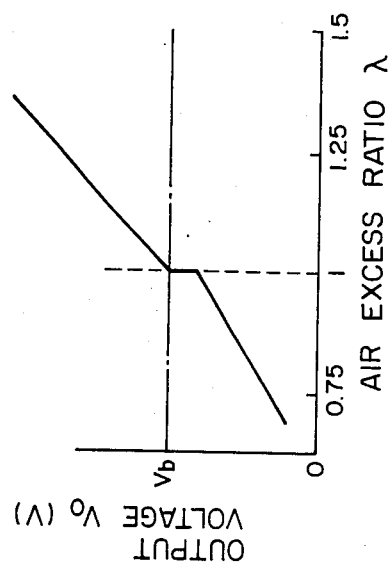

The lean and rich output voltages $e_L$ and $e_R$ are applied to the addition/subtraction circuit 36, respectively. The bias voltage $V_b$ is also applied to the addition/subtraction circuit 36. The lean output voltage $e_L$ and the bias voltage $V_b$ are applied to the (+) input terminal of the operational amplifier $A_2$, and the rich output voltage $e_R$, to the (−) input terminal of the amplifier $A_2$. Therefore, the output voltage $V_o$ of the addition/subtraction circuit 36 becomes as shown in FIG. 28. The offset voltage at the point of $\lambda=1$ is also the detection point of $\lambda=1$.

A modified example of FIG. 26 will be described with reference to FIG. 29.

Figure 26:
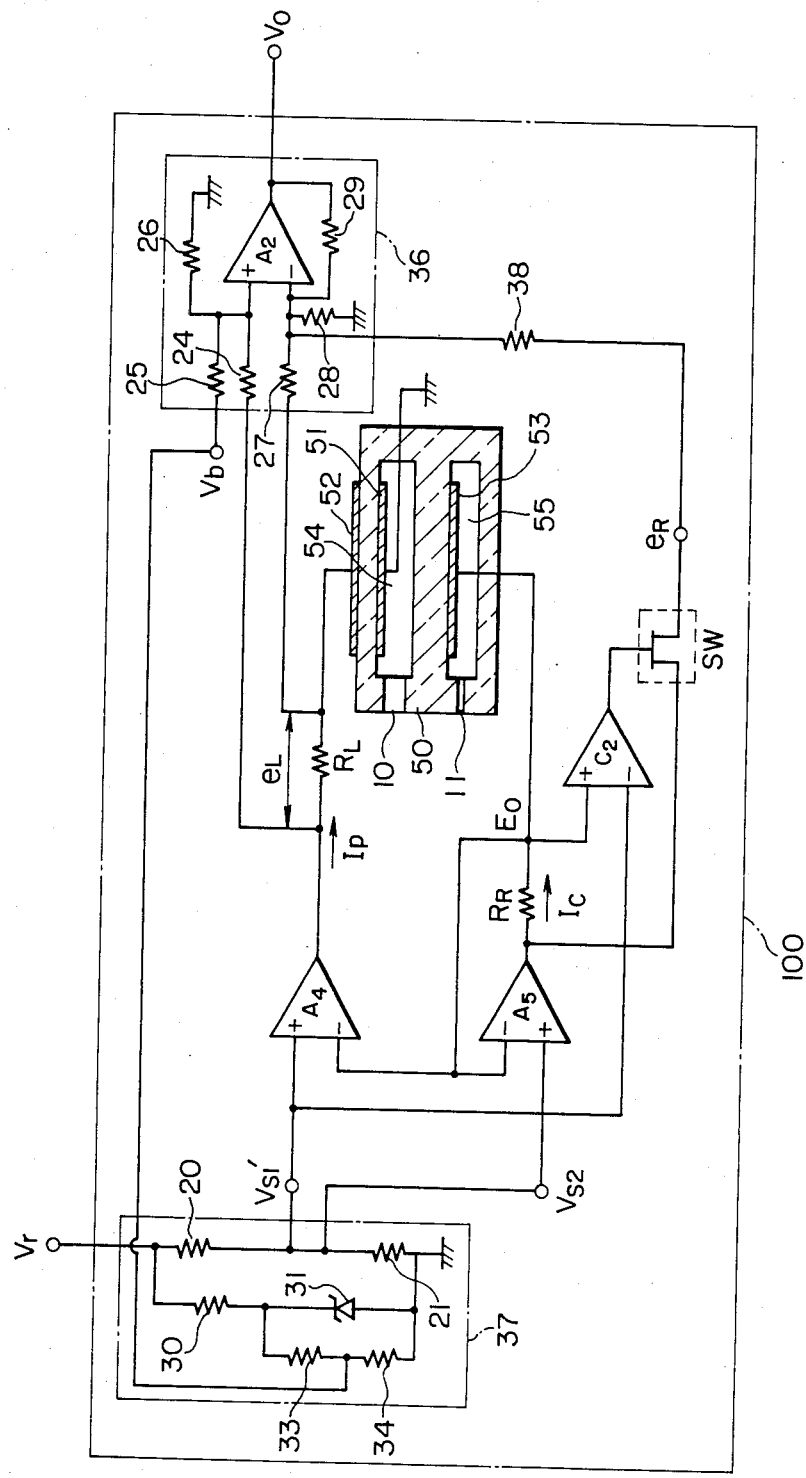
Figure 29:
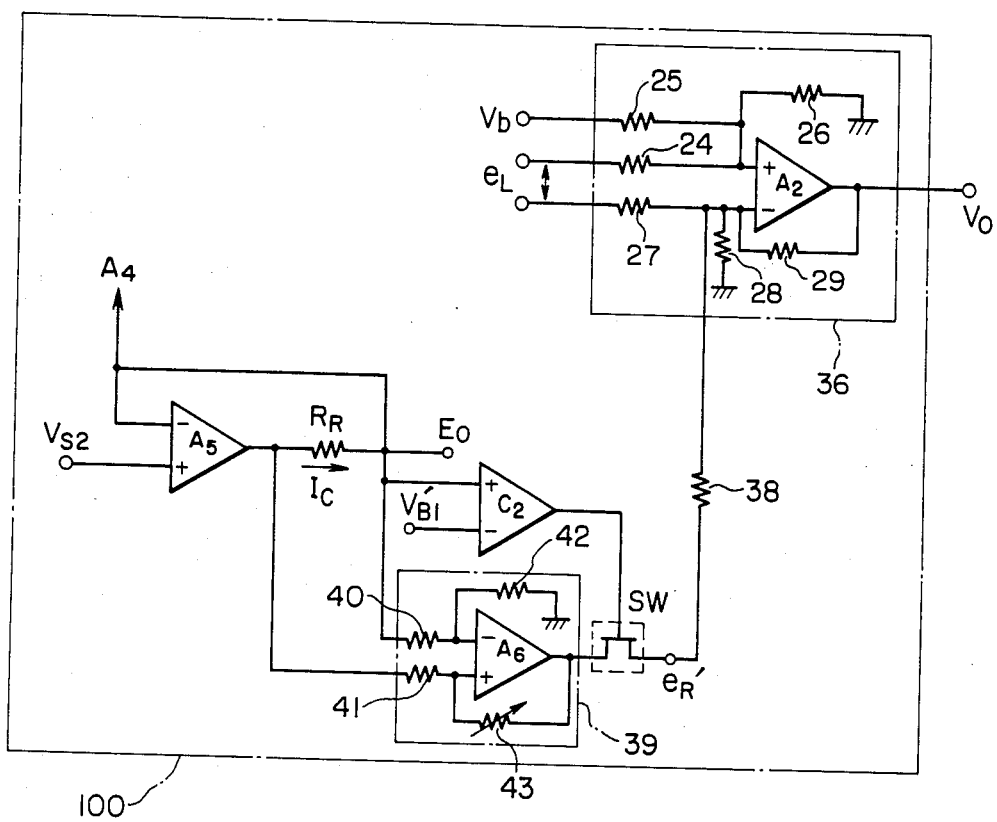
FIGS. 29 and 30 show the construction and explain the operation of still another embodiment of the present invention.
Figure 30:
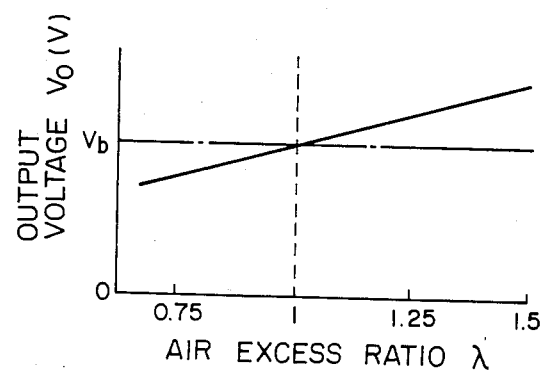

FIG. 29 shows only the principal portions of FIG. 26 and like reference numerals are used to identify like constitutents as in FIG. 26. The difference from FIG. 26 is an adjustment circuit, which consists of resistors 40 through 43 and an operational amplifier $A_6$. The (+) and (−) input terminals of the operational amplifier $A_6$ are connected to both ends of a detection resistor $R_R$. Therefore, the offset voltage $E_o$ at the point of $\lambda=1$ shown in FIG. 28 is canceled. Furthermore, the resistance of the feedback resistor 43 is variable, and can bring the inclination of the voltage $e_R$ into agreement with that of $e_L$ in FIG. 10 with respect to $\lambda$. When this adjustment circuit 39 is used, therefore, the output $V_o$ of the air-fuel ratio detector 100 becomes such as shown in FIG. 30.

The embodiments described in FIGS. 19, 26, 29, and the like provide the following effects.

(1) The air-fuel ratios in the full operating range can be detected in a wide range in those air-fuel ratio detectors which do not use an atmosphere reference or bias method and whose cells are as a whole exposed to the exhaust gas.

(2) The air-fuel ratio detector can be realized by a simple circuit to obtain an analog and linear output in accordance with a set voltage control method which changes over the polarities of the feed voltage to the air-fuel ratio detection cell in the lean and rich ranges.

(3) In accordance with the bias driving method, a simple circuit can be realized which makes it possible to control the air-fuel ratio detector by a unipolarity power source and to detect the air-fuel ratios in a wide range.

(4) The lean and rich output voltage signals including $\lambda=1$ can be standardized, and the load to peripheral circuits for controlling the engine, such as an A/D convertor, can be reduced.

What is claimed is:

1. An air-fuel ratio detector comprising:
   a solid electrolyte;
   a first electrode, a second electrode and a third electrode, each being disposed on said solid electrolyte;
   means for supplying an exhaust gas by limited diffusion to said first and third electrodes so as to provide a combined lean detecting cell and stoichiometric detecting cell construction;
   voltage supply means for supplying an exciting voltage across said first and second electrodes, whereby a lean air-fuel ratio is detected from a pumping current flowing when oxygen diffused by said exhaust gas supplying means is pumped from said first electrode to said second electrode;
   current supply means for causing a predetermined current to flow between said first and said third electrodes; and
   control means for controlling the exciting voltage supplied by said voltage supply means in accordance with a difference between the potential of said third electrode and a predetermined voltage, whereby a stoichiometric air-fuel ratio is detected from an electromotive force produced between said first and second electrodes or between said second and third electrodes when oxygen passes from said first electrode to said third electrode and said third electrode is placed under an oxygen atmosphere.

2. The air-fuel ratio detector as defined in claim 1 which further includes means for short-circuiting said first and second electrodes when the engine operates in a rich range as indicated by the potential of said third electrode becoming greater than said predetermined voltage.

3. The air-fuel ratio detector as defined in claim 1 wherein said control means further includes feedback means for making said predetermined voltage variable in accordance with the air-fuel ratio.

4. The air-fuel ratio detector as defined in claim 3 wherein said feedback means further includes oscillation prevention means for preventing transient oscillation in the controlling of said exciting voltage.

5. The air-fuel ratio detector as defined in claim 3 wherein said control means further includes means for changing stepwise said predetermined voltage at a point of stoichiometric air-fuel ratio.

6. The air-fuel ratio detector as defined in claim 1 wherein said diffusion limiting supplying means for said lean air-fuel ratio detection comprises a diffusion chamber having a slit-like diffusion path.

7. The air-fuel ratio detector as defined in claim 1 wherein said diffusion limiting supplying means for said lean air-fuel ratio detection comprises a diffusion chamber having diffusion holes of a bored hole type.

8. The air-fuel ratio detector as defined in claim 1 wherein said third electrode is covered with a porous member.

9. The air-fuel ratio detector as defined in claim 1 wherein said first electrode and said third electrode are formed on the same plane of said solid electrolyte, and are covered with porous portions having a varying diffusion resistance.

10. The air-fuel ratio detector as defined in claim 1 wherein said third electrode is disposed inside a diffusion chamber for effecting lean air-fuel ratio detection.

11. The air-fuel ratio detector as defined in claim 1 wherein said control means includes means for controlling said potential on said third electrode so that it becomes constant, and current detection means for detecting the air-ful ratio on the rich side from a current flowing into said second electrode.

12. The air-fuel ratio detector as defined in claim 11, in which said control means further includes means for cutting off the output from said current detection means when said potential on said third electrode is smaller than said predetermined voltage.

13. The air-fuel ratio detector as defined in claim 11, in which said control means further includes means for adding a predetermined value to the detection value of the current flowing to said current detection means and for reducing the detection value of said current flowing to said second electrode.

14. The air-fuel ratio detector as defined in claim 1, in which said control means further includes means for stopping the application of said exciting voltage to said second electrode for air-fuel ratio detection in the rich range.

15. The air-fuel ratio detector as defined in claim 1, in which said control means further includes means for inverting the polarity of the excitation voltage applied to said second electrode for air-fuel ratio detection in accordance with the the relationship between the potential of said third electrode and a predetermined value.

16. The air-fuel ratio detector as defined in claim 15 wherein said inversion means consists of means for switching the excitation voltage applied to said second electrode to another voltage level in accordance with the relationship between the potential of said third electrode and said predetermined value, and for applying an intermediate voltage to said first electrode.

17. The air-fuel ratio detector as defined in claim 15, in which said control means further includes means for adding a predetermined value to the voltage produced by said pumping current.

* * * * *